(12) United States Patent
Honda et al.

(10) Patent No.: US 11,896,467 B2
(45) Date of Patent: Feb. 13, 2024

(54) FOLDED INDIVIDUAL ARTICLE IN A CIRCULAR PACKAGE

(71) Applicant: Johnson & Johnson Consumer Inc., Skillman, NJ (US)

(72) Inventors: Agnes Narimatsu Honda, Sao Jose dos Campos/SP (BR); Vivian Pierri, Sao Jose dos Campos/SP (BR)

(73) Assignee: Johnson & Johnson Consumer Inc., Skillman, NJ (US)

( * ) Notice: Subject to any disclaimer, the term of this patent is extended or adjusted under 35 U.S.C. 154(b) by 1089 days.

(21) Appl. No.: 16/625,197

(22) PCT Filed: Jun. 28, 2018

(86) PCT No.: PCT/IB2018/054817
§ 371 (c)(1),
(2) Date: Dec. 20, 2019

(87) PCT Pub. No.: WO2019/003184
PCT Pub. Date: Jan. 3, 2019

(65) Prior Publication Data
US 2020/0138646 A1    May 7, 2020

Related U.S. Application Data

(60) Provisional application No. 62/527,214, filed on Jun. 30, 2017.

(51) Int. Cl.
*A61F 13/15* (2006.01)
*A61F 13/551* (2006.01)
*A61F 13/47* (2006.01)

(52) U.S. Cl.
CPC ...... *A61F 13/5514* (2013.01); *A61F 13/4704* (2013.01); *A61F 2013/4708* (2013.01)

(58) Field of Classification Search
CPC ............ A61F 13/5513; A61F 13/55135; A61F 13/5514; A61F 13/55145; A61F 13/5515;
(Continued)

(56) References Cited

U.S. PATENT DOCUMENTS 3,683,915 A     8/1972  Voss
3,971,378 A     7/1976  Krantz
(Continued)

FOREIGN PATENT DOCUMENTS

AU     2009213760 B     8/2009
EP        471384 A      2/1992
(Continued)

OTHER PUBLICATIONS

International search report dated Oct. 8, 2018, for international application PCT/IB2018/054817.
(Continued)

*Primary Examiner* — Bradley H Philips

(57) ABSTRACT

A packaged elongate sanitary protection product includes a folded sanitary product and a circular package. The sanitary product has first and second arcuate end portions comprising first and second ends, respectively, separated by a central portion, and a pair of longitudinal side edges connecting the first and second ends. The arcuate end portions have an effective radius and a maximum width, substantially equal to twice the effective radius. The central portion has a minimum width between about 75% and about 90% of the maximum width, and the sanitary product has a length between about 225% and about 285% of the maximum width. In addition, first and second fold lines are located a distance from each end equal to about 85% to about 105% of the maximum width of the arcuate end portions. The sanitary protection product is folded in a Z-configuration on first and second fold lines to form a substantially circular
(Continued)

folded sanitary protection product, which is enveloped in the circular package.

14 Claims, 5 Drawing Sheets

(58) Field of Classification Search
CPC ............ A61F 13/5516; A61F 13/55165; A61F 13/00072; A61F 13/00076; A61F 13/0008
See application file for complete search history.

(56) References Cited

U.S. PATENT DOCUMENTS

| | | |
|---|---|---|
| 4,556,146 A | 12/1985 | Swanson et al. |
| 4,560,379 A | 12/1985 | Stemmler |
| 4,650,480 A | 3/1987 | Stemmler |
| 4,674,510 A | 6/1987 | Sneider |
| 4,692,162 A | 9/1987 | Binker et al. |
| 4,765,477 A | 8/1988 | Froidh et al. |
| 4,917,675 A | 4/1990 | Taylor et al. |
| 5,827,248 A | 10/1998 | Crawford |
| 5,891,123 A | 4/1999 | Balzar |
| 6,036,679 A | 3/2000 | Balzar et al. |
| 6,293,932 B1 | 9/2001 | Balzar et al. |
| 6,502,695 B1 | 1/2003 | Kim et al. |
| 6,551,431 B2 | 4/2003 | Lee |
| 6,908,458 B1 | 6/2005 | Sauer et al. |
| 7,017,744 B2 | 3/2006 | Persson |
| 7,181,894 B2 | 2/2007 | Snell |
| 8,142,255 B2 | 3/2012 | Johnston |
| 9,242,788 B2 | 1/2016 | Gagliardi et al. |
| 9,278,035 B2 | 3/2016 | Hashino et al. |
| 2002/0063076 A1 | 5/2002 | Kolterjohn et al. |
| 2003/0163109 A1* | 8/2003 | Ohba .................. A61F 13/5611 604/385.03 |
| 2004/0250712 A1 | 12/2004 | Tippey |
| 2005/0015052 A1* | 1/2005 | Klippen ............ A61F 13/55135 604/150 |
| 2006/0100599 A1 | 5/2006 | Engel et al. |
| 2007/0078425 A1* | 4/2007 | Pateras ................ A61F 13/5514 604/385.01 |
| 2008/0077114 A1 | 3/2008 | Klippen et al. |
| 2010/0298797 A1* | 11/2010 | Ehlenbach ................ B32B 3/04 428/343 |
| 2013/0220860 A1 | 8/2013 | Bacon et al. |
| 2014/0367290 A1 | 12/2014 | Nomoto et al. |
| 2015/0313763 A1 | 11/2015 | Bagger-Sjoback et al. |
| 2016/0228309 A1* | 8/2016 | Ekstedt ............... A61F 13/5514 |

FOREIGN PATENT DOCUMENTS

| | | |
|---|---|---|
| EP | 750896 A | 1/1997 |
| EP | 754440 A | 1/1997 |
| EP | 841049 A | 5/1998 |
| EP | 1119325 A | 8/2001 |
| EP | 1324735 A | 7/2003 |
| EP | 1357877 A | 11/2003 |
| EP | 1392213 A | 3/2004 |
| EP | 1392580 A | 3/2004 |
| EP | 1793779 A | 6/2007 |
| EP | 1934102 A | 6/2008 |
| EP | 1959903 A | 8/2008 |
| EP | 2046253 A | 4/2009 |
| EP | 2379038 A | 10/2011 |
| EP | 2512943 A | 10/2012 |
| EP | 2689757 A | 1/2014 |
| EP | 2796119 A | 10/2014 |
| WO | WO 1996/020668 A | 7/1996 |
| WO | WO 1997/015261 A | 5/1997 |
| WO | WO 1998/020823 A | 5/1998 |
| WO | WO 1998/053781 A | 12/1998 |
| WO | WO 1999/052484 A | 10/1999 |
| WO | WO 2000/013622 A | 3/2000 |
| WO | WO 2000/021477 A | 4/2000 |
| WO | WO 2001/012117 A | 2/2001 |
| WO | WO 2012/102071 A | 8/2012 |
| WO | WO 2013/077789 A | 5/2013 |
| WO | WO 2013/162430 A | 10/2013 |
| WO | WO 2014/204018 A | 12/2014 |
| WO | WO 2015/060755 A | 4/2015 |

OTHER PUBLICATIONS

YouTube video clip entitled "Classic double bed mosquito net Folding method-I," Screen captures and translated transcript, 13 pages, uploaded on Jul. 3, 2016 by user "Classic mosquito net", retrieved from Internet https://www.youtube.com/watch?v=pcmyYOqzYUI.

* cited by examiner

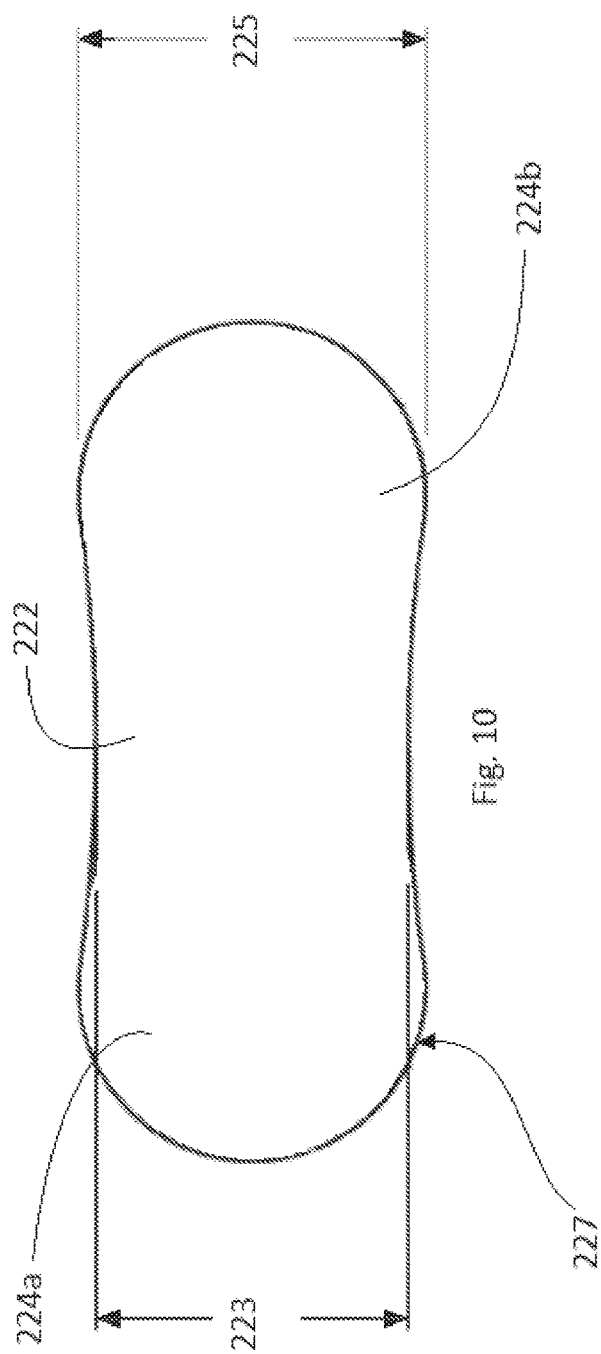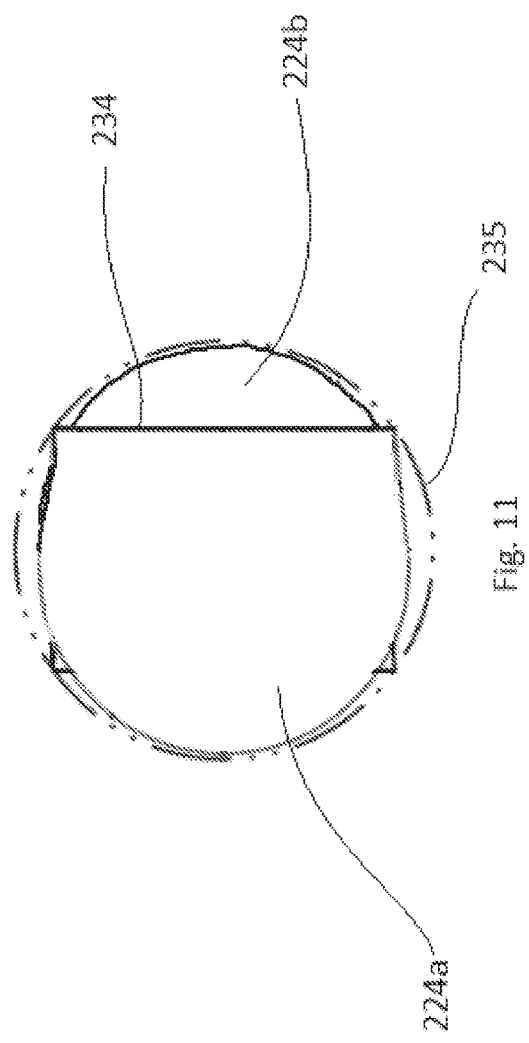

FOLDED INDIVIDUAL ARTICLE IN A CIRCULAR PACKAGE

CROSS-REFERENCE TO RELATED APPLICATIONS

This application is the national stage filing under 35 USC 371 of international application PCT/B2018/054817 filed on Jun. 28, 2018, which claims the benefit of US provisional application 62/527,214 filed on Jun. 30, 2017.

FIELD OF THE INVENTION

The present invention relates to a foldable consumer article in a single use package with a generally circular appearance. More specifically, the present invention is directed to a consumer article with circular ends folded in "Z" configurations and individually wrapped in a thin, rounded sealable package.

BACKGROUND OF THE INVENTION

Personal consumer products such as wipes, wound bandages, and absorbent articles are commonly packaged in packages containing many individual articles. Often, the consumer wishes only to carry one or several of the articles in in a pocket, small bag, or purse. For user convenience, the articles may be packaged individually in single-use packages. Typically, the package is foil or plastic material, and sealed to prevent contamination of the product.

Generally, the package is square or rectangular in geometry. In some cases, the article is folded so as to take up less space in the bag or purse.

In the case of absorbent articles such as sanitary napkins and panty liners, women will carry one or several in their bag or purse. They remove them when needed. The square or rectangular packages, however, provide a conspicuous presentation for a single wrapped and folded sanitary article, and many women desire a less conspicuous wrapper, such as a more circular product.

Unfortunately, packaging a folded sanitary product having one or more protruding square edges does not present a nice, circular product for wrapping, and it creates wasted area within a circular package; this is especially true for a folded product employing a "C-fold" or G-fold" configuration. Therefore, what is needed is a substantially circular, folded sanitary product that can be neatly and economically enveloped in a circular pouch.

SUMMARY OF THE INVENTION

Surprisingly, we have found that a sanitary product can be designed to be folded to form a substantially circular, folded sanitary product that can be neatly enveloped in a tight-fitting circular pouch.

In one embodiment of our invention, a packaged elongate sanitary protection product includes a folded sanitary protection product and a circular package. The sanitary product has first and second arcuate end portions comprising first and second ends, respectively, separated by a central portion, and a pair of longitudinal side edges connecting the first and second ends. The arcuate end portions have an effective radius, and a maximum width, substantially equal to twice the effective radius. The central portion has a minimum width between about 75% and about 90% of the maximum width of the arcuate end portions, and the sanitary protection product has a length between about 225% and about 285% of the maximum width of the arcuate end portions. In addition, first and second fold lines are located a distance from each end equal to about 85% to about 105% of the maximum width of the arcuate end portions. The sanitary protection product is folded in a Z-configuration on the first and second fold lines to form a substantially circular folded sanitary protection product, which is enveloped in the circular package.

In another embodiment, the invention relates to a method of packaging an elongate sanitary protection product, such as described above. The method includes forming a first fold, substantially perpendicular to the length of the sanitary protection product, located a distance from the first end approximately equal to about 85% to about 105% of the maximum width of the arcuate end portions, forming a second fold, substantially perpendicular to the length of the sanitary protection product, located a distance from the second end approximately equal to about 85% to about 105% of the maximum width of the arcuate end portions, and enveloping the folded sanitary protection product with packaging material to form a substantially circular package. The first and second folds are in a Z-configuration to form a substantially circular Z-folded sanitary protection product.

BRIEF DESCRIPTION OF THE DRAWINGS

FIG. 10 is a top view of an exemplary foldable sanitary protection product of the present invention.

FIG. 11 is a top view of the folded sanitary protection product of FIG. 10.

DETAILED DESCRIPTION OF THE INVENTION

The present invention relates to foldable consumer articles in a package with a generally circular appearance. The following description is presented to enable one of ordinary skill in the art to make and use the invention. Various modifications to the embodiments and the generic principles and features described herein will be readily apparent to those skilled in the art. Thus, the present invention is not intended to be limited to the embodiments shown, but is to be accorded the widest scope consistent with the features described herein.

The foldable consumer articles are first folded using two folding axes, also known as a "Z-fold", and then packaged in a thin, generally circular package.

Figure 1:
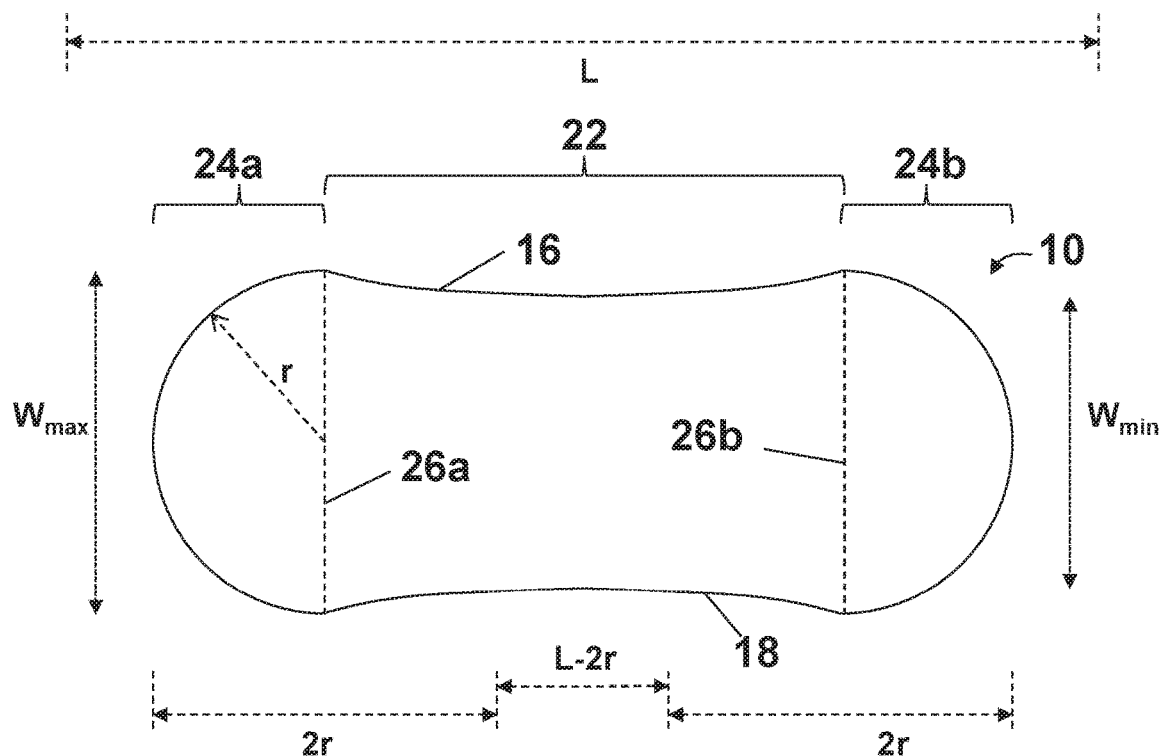
FIG. 1 is a top view of an embodiment of a foldable, round-ended consumer article of the present invention.
Figure 2:
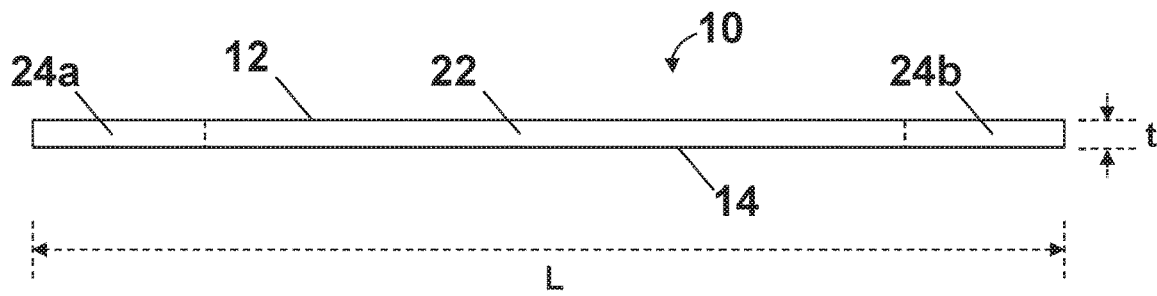
FIG. 2 is a side view of the consumer article embodiment of FIG. 1.

Referring to the drawings, FIGS. 1 and 2 are top and side views, respectively, of an embodiment of a foldable, round-ended consumer article 10 which may be used in the present invention. The article 10 has a first surface 12, a second surface 14, a first longitudinal side edge 16, and a second longitudinal side edge 18. Article 10 also has a central portion 22 and first and second arcuate end portions 24a and 24b, respectively. Article has a topsheet, a backsheet, and an absorbent structure therebetween The materials of the topsheet, backsheet, and absorbent structure may be any conventional or exotic sanitary protection materials. Optional materials, such as transfer layers, may also be included in the absorbent sanitary articles of this invention.

Consumer article 10 has dimensions of length, "L", maximum width, "$W_{max}$", minimum width, "$W_{min}$", and thickness, "t" (measured as described below). Maximum width, "$W_{max}$" and minimum width, "$W_{min}$" results in consumer article 10 having a substantially hourglass shape. In some embodiments, thickness, "t" is less than about 2 mm.

End sections 24a and 24b are arcuate, where the term "arcuate" is defined as curved in shape. FIG. 1 shows first end section 24a having an effective radius of "$r_a$", as measured from the center point of phantom line 26a which is drawn between the points on first side edge 16 and second side edge 18 where article 10 transitions from central portion 22 to first end portion 24a to any outside edge point of end portion 24a. Second end portion 24b is shown as a mirror image of first end portion 24a and has an effective radius of "$r_b$", as measured from the center point of phantom line 26b which is drawn between the points on first side edge 16 and second side edge 18 where article 10 transitions from central portion 22 to second end portion 24b to any outside edge point of end portion 24b. Side edges 16 and 18 are concave when followed from phantom line 26a to from phantom line 26b.

It is important to note that although end portions 24a and 24b project semi-circles when viewed from the top, they may also project as circular segments, semi-ellipses, or elliptical segments. If end portions 24a and 24b project as circular segments, effective radius r is measured from the center point of phantom line 26a drawn between the points on first side edge 16 and a second side edge 18 where article 10 transitions from central portion 22 to first end portion 24a to the outside edge point of end portion 24a parallel to length direction L. If end portions 24a and 24b project as semi-ellipses or elliptical segments, the long axis of the ellipse may be either parallel to, or normal to length direction L. In these cases, effective radius r is measured from the center point of phantom line 26a drawn between the points on first side edge 16 and second side edge 18 where article 10 transitions from central portion 22 to first end portion 24a to the outside edge point of end portion 24a parallel to length direction L. In all of the embodiments, end portion 24b is a mirror image of end portion 24a.

FIG. 1 shows length L of article 10 broken into three portions, the lengths of which are 2r, L−2r, and 2r. When summed together, the three lengths add up to the overall length L of consumer article 10.

Consumer article 10 is a foldable, where "foldable" is defined as capable of being folded. An item is foldable if ratio of the length L to the thickness t is greater than that calculated using the well-known Gallivan paper folding formula:

$$L \geq (\pi t(2^n+4)(2^n-1))/6,$$

where L=length,
t=thickness, and
n=the number of folds.

Since the number of folds is 1, n=1, and the ration of L to t is calculated to be:

$$L \geq \pi t/6.$$

Foldable, round-ended consumer article 10 may be any number of different consumer articles with the rounded ends and the appropriate L/t ratio. These include, but are not limited to: baby or adult wipes, wound bandages and gauze, and absorbent articles such as diapers, sanitary napkins and panty liners.

Consumer article 10 is folded prior to being packaged in a thin, cylindrical package. The folding arrangement uses two folding axes that form fold lines 28. The folding results in what is known as a "Z-fold", since the folded article has the look of a forward or reversed English letter Z as viewed from the side.

Figure 3:
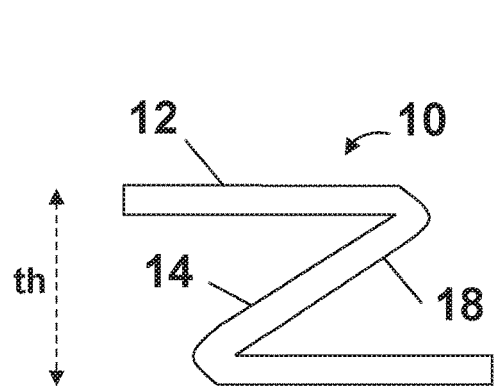
FIG. 3 is a side view of an example folding arrangement of the consumer article embodiment of FIG. 1 using two folding axes.

FIG. 3 is a side view of an example folding arrangement of first embodiment consumer article 10 using two folding axes. The figure shows first surface 12, second surface 14, and second side edge 18 of article 10. After folding, the thickness of consumer article 10 is represented by "th". The value of th will depend on the pressure used to compress the "Z" configuration of article 10. The minimum for th will be about three times the thickness (t) of consumer article 10, or $$th \geq 3t$$

Figure 4:
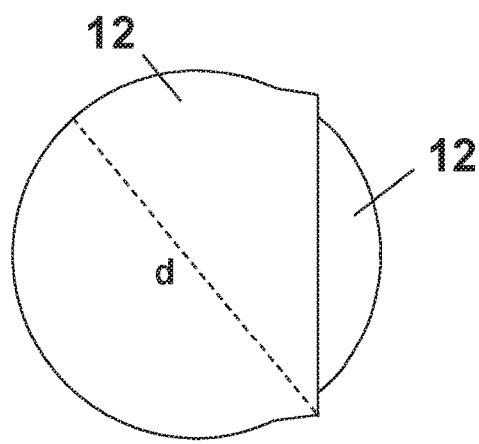
FIG. 4 is a top view of the folded consumer article of FIG. 3.

FIG. 4 is a top view of folded consumer article 10. In this view, end portions first surface 12 is visible. Diagonal "d" is calculated using the geometrical formula:

$$d \geq (5W^2 + L^2 - 4LW)^{1/2},$$

where, d=diagonal,
W=width, and
L=length.

In the embodiment shown in FIGS. 3 and 4, the length L of consumer article 10 is equal to five times the radius "r" of end portions 24a and 24b. As a result, the top view of folded consumer article 10 project as nearly circular. In some embodiments, L is greater than six times r (or 3 times $W_{max}$), while in other embodiments, L is less than six times r (or 3 times $W_{max}$).

The narrowed central portion 22 allows the Z-folded product to acquire a nearly circular format. Preferably, the central portion 22 has a minimum width ($W_{min}$) that is between about 75% and about 90% of the maximum width ($W_{max}$). More preferably, the $W_{min}$ is between about 80% and about 85% of $W_{max}$. The relationship between the article length L and maximum width $W_{max}$ also affects the ability of the Z-folded product to acquire the desired nearly circular format. Preferably, the article length L is between about 225% and about 285% of the maximum width ($W_{max}$). More preferably, L is between about 235% and 250% of $W_{max}$. In addition, the location of the fold lines 28a, 28b affects the ability of the Z-folded product to acquire the desired nearly circular format. Preferably, the fold lines 28a, 28b are located a distance from each end 24a, 24b, respectively, equal to about 85% to about 105% of the $W_{max}$, more preferably, between about 90% to about 95% of the $W_{max}$.

Figure 5:
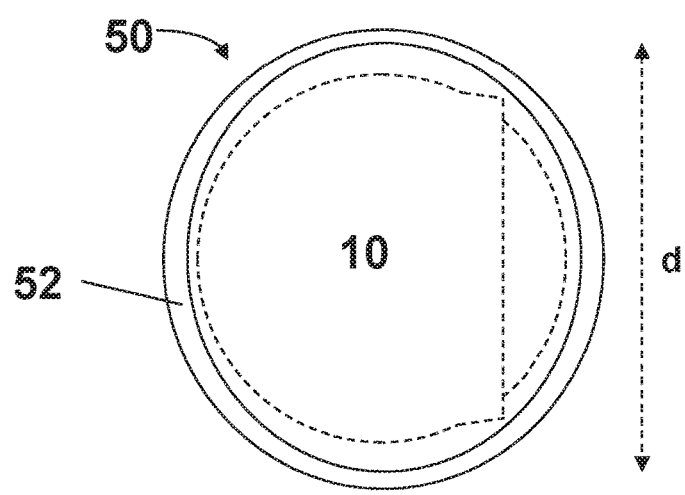
FIG. 5 is a top view of the folded consumer article of FIG. 4 wrapped in thin, cylindrical package.

FIG. 5 is a top view of the folded consumer article 10 of FIG. 4 wrapped in thin, circular package, where "thin" is defined as a folded consumer article 10 thickness th to diagonal d ratio (th/d) of less than 0.5, or 0.25, or 0.1 or 0.05. FIG. 5 shows the inner diameter of circular package 50 equal to diagonal d. Circular package 50 is also shown to have circular flange seal 52 to prevent contamination to folded consumer article 10.

It is important to note that circular package 50 could also be in the form of an elliptical or oval cylindrical package, where the top view of the package projects an ellipse or an oval. Package 50 must also have an internal volume sized to receive folded consumer article 10.

Circular package 50 could be made of sealable materials such as thin aluminum foil or plastic film. In the case of aluminum foil, the package can be sealed via crimp sealing. Plastic film material can be sealed via heat sealing. In some embodiments, the packing material is two sheets of packing material. In other embodiments, the packing material is a folded sheet of packing material.

Figure 6:
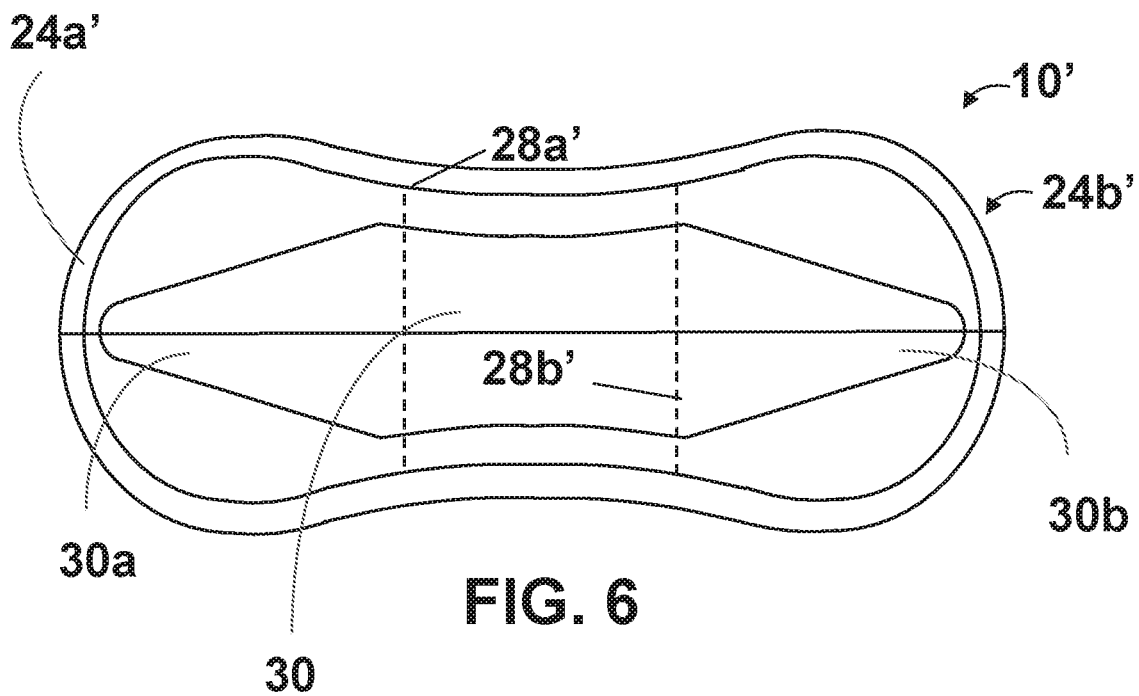
FIG. 6 is a top view of a second embodiment of a foldable, round-ended consumer article of the present invention.
Figure 7:
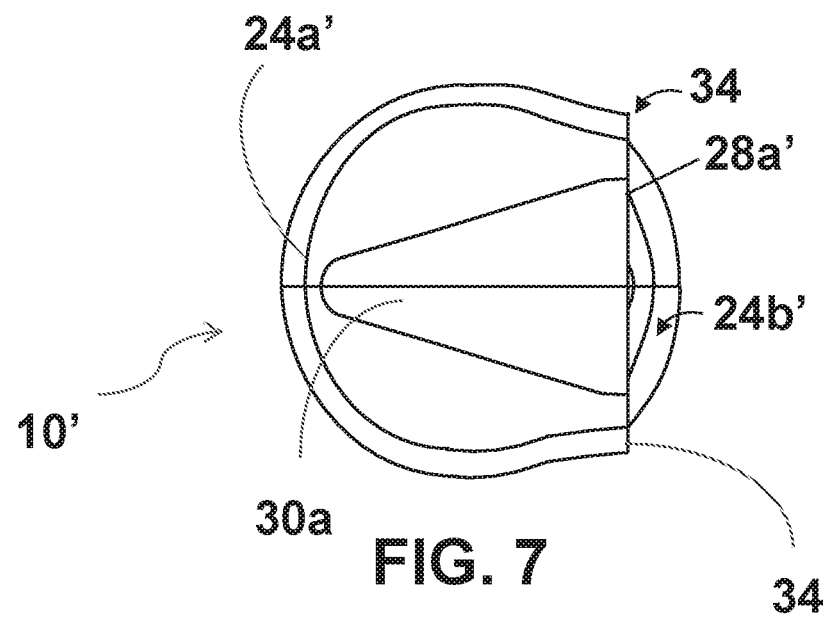
FIG. 7 is a top view of the folded consumer article of FIG. 6.

In a preferred embodiment, shown in FIG. 6, the first fold line 28a' is disposed perpendicular to the longitudinal axis and is located at a distance from the first end 24a' approximately equal to the maximum width $W_{max}$ of the first end 24a'. The second fold line 28b' is also disposed perpendicular to the longitudinal axis and is located at a distance from the second end 24b' approximately equal to the maximum width $W_{max}$ of the second end 24b'. Thus, when the product is folded in the Z-fold configuration, as shown in FIG. 7, the arcuate ends 24a', 24b' of the sanitary protection article 10' define a substantially circular Z-folded sanitary protection product. In this embodiment, the absorbent core 30 has narrowed ends 32a and 32b and does not extend over the total area of the absorbent article 10'. The circular form of the ends 24a', 24b' and the location of the fold lines 28a', 28b' provide a substantially circular folded product with minor protruding square edges 34.

Thickness Measurement:

Thickness of the product can be determined with a thickness gauge applying uniform pressure. A preferred thickness gauge is Ames LG 1820-1-04 or equivalent with a 0.1 psi pressure applied by a 57 g dead weight and a foot surface area of 1.129" of diameter contact; precision is ±0.02 mm or 0.001". The product thickness is measured in the first and second ends and in the center portion. The thickness of the finished product (less any release paper) is measured as follows:
1. Place the release paper (if any) under the foot of the thickness gauge.
2. Re-zero the gauge to remove the thickness of the release paper from the measurements. The gauge should read 0.00 mm (0.000").
3. Reposition the release paper so that it is positioned properly on the adhesive strip and that there are no folds in it, if necessary.
4. Raise the foot of the gauge and place the napkin underneath at the desired position (first and second ends and in the center portion) so that the foot of the gauge hangs above the product.
5 Lower the foot delicately, making sure it does not drop suddenly on the product surface.
6 Allow the gauge to stabilize (approximately 3 seconds), and record the product thickness to the nearest 0.02 mm (0.001").
7 Repeat steps 4 to 6 for each product area to be measured.

EXAMPLES

Example 1

Figure 8:
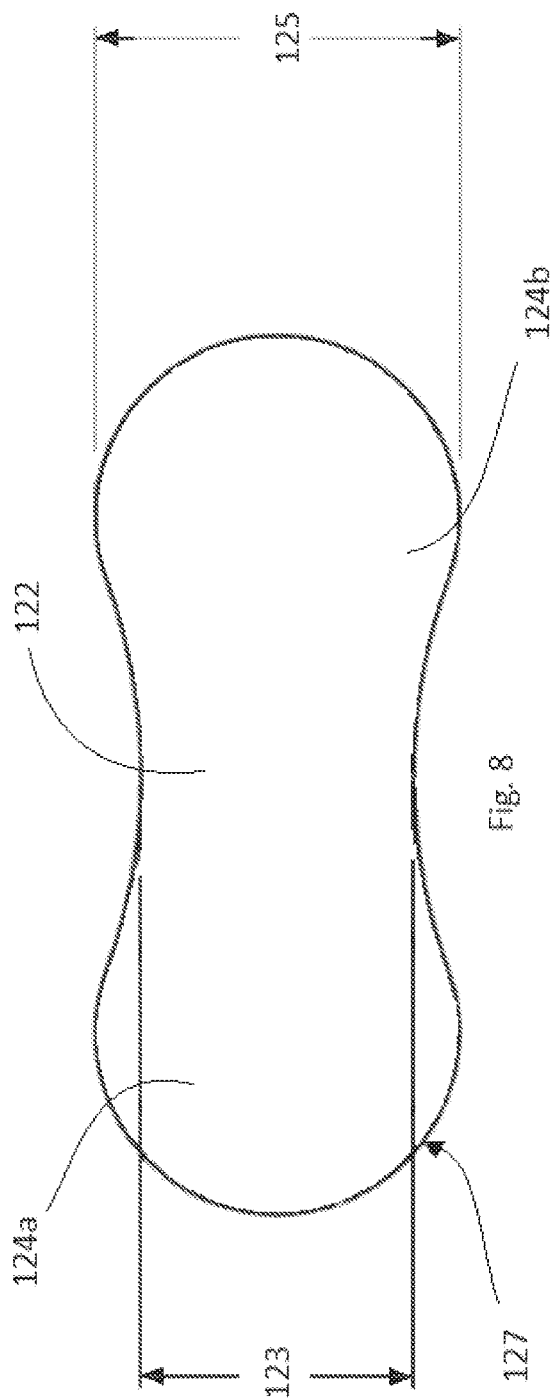
FIG. 8 is a top view of an exemplary foldable sanitary protection product of the present invention.
Figure 9:
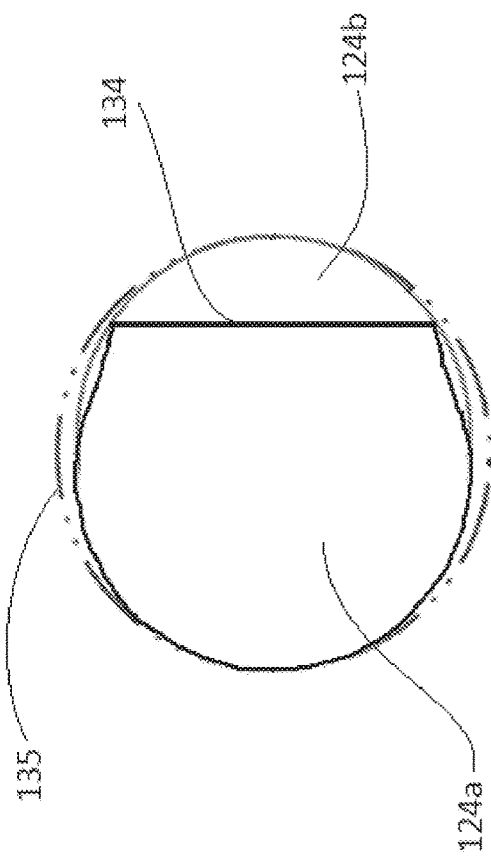
FIG. 9 is a top view of the folded sanitary protection product of FIG. 8.

An example of a pantiliner 110 according to the invention is shown in FIGS. 8 and 9. As shown in the top plan view, the arcuate ends 124a, 124b have a maximum width 125 of 58 mm and a radius 127 of 25 mm, and the central portion 122 has a minimum width 123 of 43.5 mm. Thus, the central portion 122 has a minimum width of about 75% of the maximum width of the arcuate ends 124a, 124b. When the product is z-folded along fold lines 134 as shown in FIG. 9, with the first arcuate end 124a on top, the product can be circumscribed by a circle 135 having a diameter of 64 mm.

Example 2

An example of a pantiliner 210 according to the invention is shown in FIGS. 10 and 11. As shown in the top plan view, the arcuate ends 224a, 224b have a maximum width 225 of 58 mm and a radius 227 of 27 mm, and the central portion 222 has a minimum width 223 of 52.2 mm. Thus, the central portion 222 has a minimum width of about 90% of the maximum width of the arcuate ends 224a, 224b. When the product is z-folded along fold lines 234 as shown in FIG. 11, with the first arcuate end 224a on top, the product can be circumscribed by a circle 235 having a diameter of 64 mm.

The specification and embodiments above are presented to aid in the complete and non-limiting understanding of the invention disclosed herein. Since many variations and embodiments of the invention can be made without departing from its spirit and scope, the invention resides in the claims hereinafter appended.

What is claimed is:
1. A packaged elongate sanitary protection product comprising:
  a) the sanitary protection product having:
    i) first and second arcuate end portions comprising first and second ends, respectively, separated by a central portion, the arcuate end portions having an effective radius;
    ii) a pair of longitudinal side edges connecting the first and second ends;
    iii) first and second arcuate ends having maximum width substantially equal to twice the effective radius;
    iv) the central portion having a minimum width between about 75% and about 90% of the maximum width;
    v) the sanitary protection product having a length between about 225% and about 285% of the maximum width; and
    vi) first and second fold lines located a distance from each end equal to about 85% to about 105% of the maximum width;
  wherein the sanitary protection product is folded in a Z-configuration on the first and second fold lines to form a substantially circular folded sanitary protection product; and
  b) a circular package arranged and configured to envelope the substantially circular Z-folded sanitary protection product.

2. The packaged elongate sanitary protection product having a substantially hourglass shape.

3. The packaged elongate sanitary protection product of claim 2, wherein the pair of longitudinal side edges in the central portion are substantially concave.

4. The packaged elongate sanitary protection product of claim 3, wherein the pair of longitudinal side edges have a substantially curvilinear transition from the substantially arcuate ends to the substantially concave central portion.

5. The packaged elongate sanitary protection product of claim 1, wherein the sanitary protection product has a length between about 235% and about 250% of the maximum width.

6. The packaged elongate sanitary protection product of claim 1, wherein the first and second fold lines are located a distance from each end equal to about 90% to about 95% of the maximum width.

7. The packaged elongate sanitary protection product of claim 1, wherein the circular package comprises a substantially circular flange seal.

8. The packaged elongate sanitary protection product of claim 7 wherein the packaging material comprises two sheets of packaging material.

9. The packaged elongate sanitary protection product of claim 7 wherein the packaging material comprises a folded sheet of packaging material.

10. The packaged elongate sanitary protection product of claim 1 wherein the sanitary protection product has a thickness of less than about 2 mm.

11. A method of packaging an elongate sanitary protection product comprising first and second arcuate end portions comprising first and second ends, respectively, separated by a central portion, the arcuate end portions having an effective radius and a maximum width substantially equal to twice the effective radius, a pair of longitudinal side edges connecting the first and second ends, wherein the central portion has a minimum width between about 75% and about 90% of the maximum width, the sanitary protection product has a length between about 200% and about 300% of the maximum width, the method comprising the steps of:
  a) forming a first fold, substantially perpendicular to the length of the sanitary protection product, located a distance from the first end approximately equal to the maximum width;
  b) forming a second fold, substantially perpendicular to the length of the sanitary protection product, located a distance from the second end approximately equal to the maximum width;
whereby the first and second folds are in a Z-configuration to form a substantially circular Z-folded sanitary protection product; and
  c) enveloping the substantially circular Z-folded sanitary protection product with packaging material;
  d) forming a substantially circular flange seal in the packaging material to envelope the Z-folded sanitary protection product.

12. The method of claim 11 wherein the sealed packaging material is substantially circular.

13. The method of claim 11 wherein the packaging material comprises two sheets of packaging material.

14. The method of claim 11 wherein the packaging material comprises a folded sheet of packaging material.

* * * * *